United States Patent
Tatsumi et al.

(10) Patent No.: US 10,045,948 B2
(45) Date of Patent: Aug. 14, 2018

(54) PRAMIPEXOLE-CONTAINING TRANSDERMAL PATCH FOR TREATMENT OF NEURODEGENERATIVE DISEASE

(71) Applicant: MEDRX CO., LTD., Kagawa (JP)

(72) Inventors: Noboru Tatsumi, Kagawa (JP); Makiko Takemoto, Kagawa (JP); Hidetoshi Hamamoto, Kagawa (JP)

(73) Assignee: MEDRX CO., LTD., Kagawa (JP)

( * ) Notice: Subject to any disclaimer, the term of this patent is extended or adjusted under 35 U.S.C. 154(b) by 0 days.

(21) Appl. No.: 15/121,851

(22) PCT Filed: Feb. 18, 2015

(86) PCT No.: PCT/JP2015/054493
§ 371 (c)(1),
(2) Date: Aug. 26, 2016

(87) PCT Pub. No.: WO2015/129527
PCT Pub. Date: Sep. 3, 2015

(65) Prior Publication Data
US 2017/0014353 A1    Jan. 19, 2017

(30) Foreign Application Priority Data

Feb. 27, 2014    (JP) .................... 2014-037584

(51) Int. Cl.
| | |
|---|---|
| A61K 9/70 | (2006.01) |
| A61K 31/428 | (2006.01) |
| A61K 47/10 | (2017.01) |
| A61K 47/12 | (2006.01) |
| A61K 47/14 | (2017.01) |

(52) U.S. Cl.
CPC .......... *A61K 9/7023* (2013.01); *A61K 9/7053* (2013.01); *A61K 9/7069* (2013.01); *A61K 31/428* (2013.01); *A61K 47/10* (2013.01); *A61K 47/12* (2013.01); *A61K 47/14* (2013.01)

(58) Field of Classification Search
CPC .................... A61K 9/7023; A61K 31/428
See application file for complete search history.

(56) References Cited

U.S. PATENT DOCUMENTS

| | | | |
|---|---|---|---|
| 5,112,842 A | | 5/1992 | Zierenberg et al. |
| 8,623,387 B2 * | | 1/2014 | Yamaguchi .......... A61K 9/0014 |
| | | | 424/401 |
| 2004/0253299 A1 | | 12/2004 | Beier et al. |
| 2006/0182791 A1 | | 8/2006 | Theobald et al. |
| 2007/0225379 A1 | | 9/2007 | Carrara et al. |
| 2010/0256174 A1 | | 10/2010 | Yamaguchi et al. |
| 2015/0174249 A1 | | 6/2015 | Hamamoto et al. |

FOREIGN PATENT DOCUMENTS

| | | |
|---|---|---|
| AU | 2003233233 B2 | 11/2003 |
| CN | 103610666 A | 3/2014 |
| JP | H03-170425 A | 7/1991 |
| JP | 2005-528413 A | 9/2005 |
| JP | 2006-528144 A | 12/2006 |
| JP | 2008-514376 A | 5/2008 |
| JP | 2012-219044 A | 11/2012 |
| WO | 2006/039532 A2 | 4/2006 |
| WO | 2009/066457 A1 | 5/2009 |
| WO | 2011/111384 A1 | 9/2011 |
| WO | 2013/191187 A1 | 12/2013 |

OTHER PUBLICATIONS

Diao et al. Mol Pharm. Aug. 2, 2010; 7(4): 1342-1347.*
International Search Report issued in corresponding International Patent Application No. PCT/JP2015/054493 dated Apr. 14, 2015.
International Preliminary Report on Patentablity and Written Opinion issued in corresponding International Patent Application No. PCT/JP2015/054493 dated Aug. 30, 2016.
Extended European Search Report issued in corresponding European Patent Application No. 15754609.4 dated Feb. 9, 2017.

* cited by examiner

*Primary Examiner* — Shirley V Gembeh
(74) *Attorney, Agent, or Firm* — Morgan, Lewis & Bockius LLP

(57) ABSTRACT

The purpose of the present invention is to provide a non-aqueous tape that is stable and has high percutaneous absorption performance, and that contains pramipexole hydrochloride, which is slightly soluble in organic solvents and has high crystallinity. The present invention could produce a nonaqueous tape that is stable and has high percutaneous absorption performance by dissolving pramipexole, using a combination of a fatty acid ionic liquid and a divalent alcohol and a fatty acid ester. As a result, it has become possible to provide a transdermal patch (tape) containing pramipexole for the treatment of Parkinson's disease with which the problems associated with a conventional water-containing poultice of discoloration of the preparation and stability of the pramipexole can be solved.

15 Claims, 3 Drawing Sheets

PRAMIPEXOLE-CONTAINING TRANSDERMAL PATCH FOR TREATMENT OF NEURODEGENERATIVE DISEASE

TECHNICAL FIELD

The present invention relates to transdermal patch containing pramipexole that is used to treat neurodegenerative diseases (such as Parkinson's disease or restless legs syndrome).

BACKGROUND ART

Parkinson's disease is one of the more common neurodegenerative diseases along with Alzheimer's disease. The prevalence of Parkinson's disease in Japan is currently about 150 persons for every 100,000 members of the population. This disease is known to be associated with four major symptoms consisting of tremors, akinesia, muscle rigidity and postural reflex disorders. Various disorders referred to as non-motor disorders also appear in addition to motor disorders. Namely, examples of these include autonomic nervous system disorders such as constipation, frequent urination (overactive bladder) or orthostatic hypotension (fainting), sensory disorders such as lower back pain or lower extremity pain, REM sleep behavior disorders (RBD) causing dream enactment such as calling out while sleeping or not being fully awake, olfactory disorders, depression, cognitive impairment, hallucinations and delusions occurring at various times and in various combinations.

Although motor symptoms of Parkinson's disease occur due to degenerative loss of dopaminergic neurons in the substantia nigra of the mesencephalon, there is also systemic degenerative loss in several central nervous systems such as the choline system, serotonin system or noradrenaline system. Degeneration also occurs in the peripheral autonomic nervous system, giving rise to a diverse range of clinical symptoms. Disturbances first begin in the peripheral nervous system followed by continuing to progress upward while involving such tissues as the medulla oblongata, pons (RBD) or locus coeruleus (responsible for some forms of depression), eventually resulting in the presentation of the motor disorders uniquely associated with Parkinson's disease at the point the substantia nigra of the encephalon has been impaired. Moreover, disturbances such as hallucinations, delusions and cognitive impairment appear once those disturbances extend to the cerebrum. Approximately half of all patients follow this type of ascending progression.

On the other hand, restless legs syndrome (RLS) is also referred to as "itchy legs syndrome" or "twitching legs syndrome". RLS is not well known and may be easily overlooked in routine examinations. The prevalence of RLS in Japan is 2% to 5%, and about 2 million to 3 million patients are said to have this condition to an extent that it impairs their daily lives. The estimated number of patients in the U.S. and Europe is said to account for 5% to 15% of the population. This disease is said to have a predilection for persons in their forties and older, and frequently occurs in women (1.2 times to 1.4 times more frequently than in men). Due to the current low level of awareness of this disease, many patients are overlooked or diagnosed with insomnia or other illness, preventing them from receiving adequate treatment. Symptoms are particularly exacerbated when at rest during the night, and especially during sleeping hours. This is a chronic disease that progresses gradually with age, and 35% of sleep and arousal disorders in persons in their sixties are said to be caused by this disease. Although the cause of RLS is unclear, possible causes include decreased dopamine function, metabolic abnormalities caused by iron deficiency in the central nervous system, abnormalities of the spinal cord or peripheral nerves, and genetic factors.

First-line drugs used in the treatment of Parkinson's disease consist of L-dopa and dopamine agonists (dopamine receptor agonists). L-dopa demonstrates potent effects for improving motor symptoms and generally has few adverse reactions. However, it is also susceptible to the occurrence of motor complications. In contrast, although dopamine agonists are comparable to L-dopa in terms of their ameliorative effects in mild cases, they have been reported to be frequently associated with adverse reactions such as digestive symptoms or psychological symptoms to the same extent as L-dopa in advanced cases.

Benzodiazepine-based sedatives (such as clonazepam) are mainly used as first-line drugs for the treatment of mild cases of restless legs syndrome. Dopamine receptor agonists used for the treatment of Parkinson's disease (such as pramipexole or ropinirole) and dopamine preparations (such as levodopa) are considered to be effective in moderate and severe cases.

However, although dopamine receptor agonists are effective, they are known to cause nausea, vomiting, dizziness, hypotension, constipation and insomnia during initial administration.

The development of dopamine receptor agonists in the form of extended-release preparations has been considered as one way of elimination of these adverse reactions, while attempts to develop external preparations have also been made (Patent Documents 1, 2 and 3).

At present, transdermal products based on percutaneous absorption of the dopamine receptor agonist, rotigotine, have been released in the U.S. and Europe. However, adverse drug reactions in the form of rash and other types of inflammation at the application site have been reported to occur in about 40% to 50% of patients using these products. A transdermal patch that can be applied for a long period of time while avoiding these adverse reactions has yet to be found. Consequently, instead of oral preparations, a transdermal patch that can be applied over a long period of time is being sought for dopamine receptor agonists (such as pramipexole) that are effective in oral administration.

CITATION LIST

Patent Documents

[Patent Document 1] JP-A-2005-528413
[Patent Document 2] JP-A-2006-528144
[Patent Document 3] JP-A-2008-514376

SUMMARY OF INVENTION

Technical Problem

An object of the present invention is to provide a transdermal patch containing pramipexole for use as an effective therapeutic agent for neurodegenerative diseases.

Solution to Problem

The inventors of the present invention examined the production of a transdermal patch using an inorganic acid salt of pramipexole such as a hydrochloride thereof. The production of a tape preparation was examined in consideration of adhesion to skin. The active ingredient in the form of pramipexole hydrochloride has favorable crystallinity, and it was therefore difficult dissolve pramipexole in solvents ordinarily used to produce transdermal patches. Therefore, it is necessary to dissolve the pramipexole using water in order to produce a transdermal patch, and as a result thereof, there were many cases in which aqueous tape preparations were produced.

Since the base (plaster) used in tape preparations is liposoluble, if water is used to dissolve the active ingredient, water present in the tape preparation ends up dissociating from the plaster over time since water is not compatible with the plaster. Thus, the question of how to dissolve poorly soluble pramipexole in an organic solvent presented a considerable problem.

The inventors of the present invention found that a nonaqueous tape preparation can be produced by using an ionic liquid of a fatty acid having 14 to 18 carbon atoms as a solvent for dissolving pramipexole in an organic solvent and using this in combination with a divalent alcohol and fatty acid ester. Moreover, it was found that percutaneous absorption is improved considerably by adding a filler in order to improve the extended release of drug from the plaster.

The inventors of the present invention completed the subject invention on the basis of the aforementioned findings.

The gist of the present invention is as indicated below.
(1) A tape preparation comprising pramipexole and/or a pharmacologically acceptable salt thereof, a C14-C18 fatty acid-based ionic liquid, a divalent alcohol and a fatty acid ester.
(2) The tape preparation described in (1) above, wherein the fatty acid of the C14-C18 fatty acid-based ionic liquid is one or more fatty acids selected from isostearic acid, oleic acid, palmitic acid, myristic acid and stearic acid.
(3) The tape preparation described in (1) above, wherein the fatty acid of the C14-C18 fatty acid-based ionic liquid is oleic acid or myristic acid.
(4) The tape preparation described in (1) above, wherein the fatty acid of the C14-C18 fatty acid-based ionic liquid is a mixture of two types of fatty acids consisting of isostearic acid and oleic acid.
(5) The tape preparation described in any of (1) to (3) above, wherein an alkanolamine compound of the fatty acid-based ionic liquid is one or more alkanolamine compounds selected from diisopropanolamine, triethanolamine, triisopropanolamine and trometamol.
(6) The tape preparation described in any of (1) to (3) above, wherein the alkanolamine compound of the fatty acid-based ionic liquid is diisopropanolamine.
(7) The tape preparation described in any of (1) to (6) above, wherein the divalent alcohol is one or more divalent alcohols selected from propylene glycol, polyethylene glycol and 1,3-butanediol.
(8) The tape preparation described in any of (1) to (7) above, wherein the divalent alcohol is propylene glycol.
(9) The tape preparation described in any of (1) to (8) above, wherein the fatty acid ester is one or more fatty acid esters selected from diethyl sebacate, isopropyl myristate, propylene carbonate and diisopropyl adipate.
(10) The tape preparation described in any of (1) to (8) above, wherein the fatty acid ester is diethyl sebacate and/or isopropyl myristate.
(11) The tape preparation described in any of (1) to (10) above to which is added a filler.
(12) The tape preparation described in (11) above, wherein the filler is an organic filler.
(13) The tape preparation described in (11) above, wherein the organic filler is crystalline cellulose.
(14) The tape preparation described in any of (1) to (13) above, wherein the pramipexole and/or pharmacologically acceptable salt thereof is pramipexole dihydrochloride.
(15) The tape preparation described in any of (1) to (14) above, wherein the tape preparation is a nonaqueous tape preparation.
(16) The tape preparation described in any of (1) to (15) above, wherein the content of the fatty acid-based ionic liquid is 4.5% by weight to 15% by weight of an adhesive layer.
(17) The tape preparation described in any of (1) to (15) above, wherein the content of the fatty acid-based ionic liquid is 0.2 parts by weight to 0.7 parts by weight based on a value of 1 for the amount of plaster.
(18) The tape preparation described in any of (1) to (15) above, wherein the amount of plaster is 10% by weight to 50% by weight of an adhesive layer.
(19) The tape preparation described in any of (1) to (15) above, wherein the amount of plaster is 20% by weight to 45% by weight of an adhesive layer.
(20) The tape preparation described in any of (1) to (15) above, wherein the composition of the plaster consists of 1/4 parts by weight to 7/2 parts by weight of a tackifier based on a value of 1 for SIS.
(21) The tape preparation described in any of (1) to (15) above, wherein the composition of the plaster consists of 1/3 parts by weight to 5/2 parts by weight of a tackifier based on a value of 1 for SIS.
(22) The tape preparation described in any of (1) to (14) above, wherein the content of the fatty acid-based ionic liquid is 3 times to 20 times based on a value of 1 for the active ingredient in the form of pramipexole.
(23) The tape preparation described in any of (1) to (14) above, wherein the amount used of the fatty acid-based ionic liquid is 4 times to 16 times based on a value of 1 for the active ingredient in the form of pramipexole.

Advantageous Effects of Invention

The tape preparation of the present invention relates to a tape preparation containing a salt of pramipexole having favorable crystallinity. In general, salts of pramipexole (such as hydrochlorides) are poorly soluble in organic solvent and easily precipitate in the base of a nonaqueous tape preparation, thereby making it difficult to produce in the form of a tape preparation. However, in the tape preparation of the invention of the present application, crystal precipitation can be avoided by using a C14-C18 fatty acid-based ionic liquid (alkanolamine salt) as a solvent of pramipexole, thereby enabling the production of a stable tape preparation having superior percutaneous absorption. In addition, pramipexole is normally in the form of a hydrochloride and yellowing progresses when the hydrochloric acid is removed. For this reason, aqueous tape preparations thereof are susceptible to the occurrence of yellowing. However, in the nonaqueous tape preparation of the invention of the present application, there is hardly any degradation or yellowing of pramipexole observed even when stored for a long period of time.

Moreover, in the invention of the present application, drug release channels are formed in the plaster by adding organic filler. As a result, the drug can be favorably released from inside the plaster, the amount of drug that permeates the skin is greatly improved, and the amount of drug that remains in the plaster is reduced.

As a result thereof, a stable tape preparation having improved percutaneous absorption is able to be provided that uses pramipexole hydrochloride having favorable crystallinity and avoids precipitation of crystals in the tape preparation.

BRIEF DESCRIPTION OF DRAWINGS

In FIG. 1, the initial (2 to 6 hours) skin permeation rates increased to a greater extent for those tape compositions having higher skin permeation amounts. This is thought to be because the rate-determining factor of skin absorption is the main factor (dominant factor) in the case of observing skin permeation amount for 24 hours.

DESCRIPTION OF EMBODIMENTS

Figure 1:
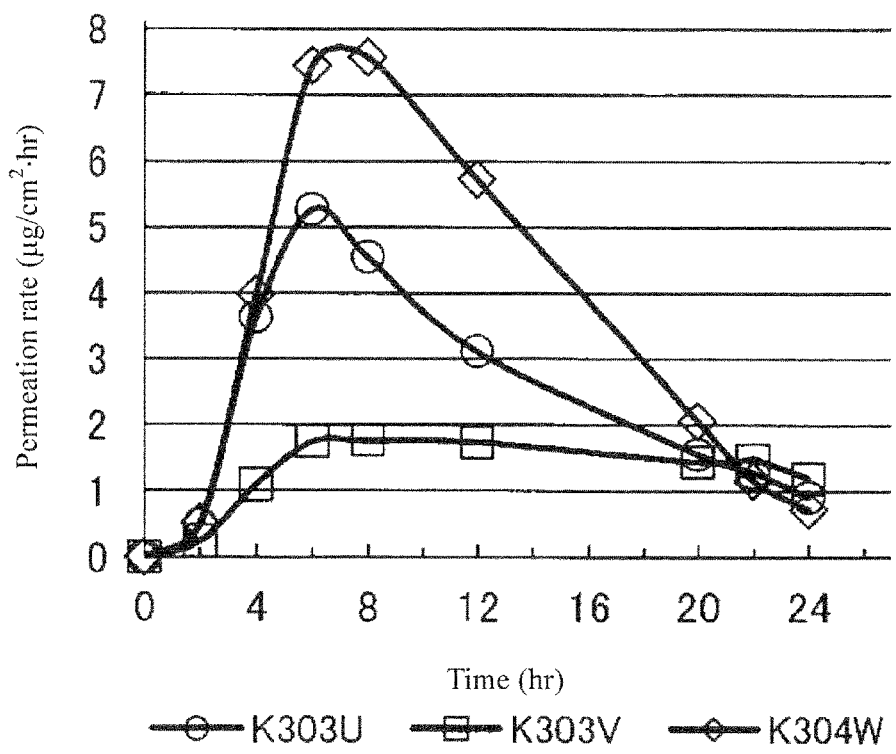
FIG. 1 is a graph representing changes in skin absorption rates at various times of three samples of test nos. K303U, K303V and K304W. Skin permeation rates reached a maximum at 6 to 8 hours after application. This is because, although drug contained in the plaster that contacts the skin is easily released, drug present in other portions of the plaster takes some time to be released. As a result, skin absorption is the rate-determining factor through 6 hours after application, and this is thought to enable the percutaneous absorption effects of the ionic liquid containing the drug and the solvent composition to be easily reflected. On the other hand, starting at 8 hours after application, the release of drug from within the plaster becomes the rate-determining factor, and the supply of drug to the plaster surface (skin surface) decreases. Consequently, the skin absorption rate appears as if to decrease.

The "pramipexole and/or pharmacologically acceptable salt thereof" of the present invention refers to (S)-2-amino-4,5,6,7-tetrahydro-6-(propylamino) benzothiazole or a pharmacologically acceptable salt thereof. A hydrochloride is typically used for the pharmacologically acceptable salt, and the "pramipexole and/or pharmacologically acceptable salt thereof" is used as a therapeutic agent for Parkinson's disease (under the trade name Bi-Sifrol or Mirapex). Furthermore, the chemical formula of Bi-Sifrol and Mirapex is that of the dihydrochloride indicated below.

[Chemical 1]

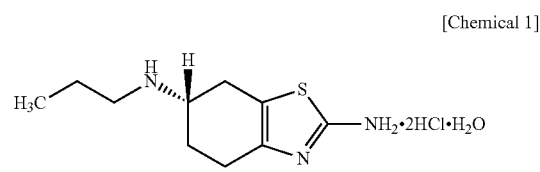

The "C14-C18 fatty acid-based ionic liquid" of the present invention refers to an equimolar salt of each of the fatty acids of myristic acid (C14), palmitic acid (C16), oleic acid (C18), isostearic acid (C18) and stearic acid (C18) and each of the alkanolamines of diethanolamine, diisopropanolamine, triethanolamine and triisopropanolamine, and the majority are in liquid form at normal temperature (room temperature: 25° C.). In addition, these fatty-acid based ionic liquids include one or more types thereof. Preferable examples of C14-C18 fatty acids include myristic acid (C14), palmitic acid (C16), oleic acid (C18) and isostearic acid (C18). Preferable examples of alkanolamines include triethanolamine and diisopropanolamine. Most preferably, examples of fatty acid-based ionic liquids include diisopropanolamine myristate and diisopropanolamine oleate. In the present invention, a combination of a plurality of types of ionic liquids is preferable, and a plurality of ionic liquids is preferably combined consisting primarily of diisopropanolamine myristate and diisopropanolamine oleate.

The content of the fatty acid-based ionic liquid of the invention of the present application based on a value of 1 for the amount used of the active ingredient in the form of pramipexole is preferably 1.0 times or more from the viewpoint of pramipexole solubility and percutaneous absorption, and preferably 20 times or less in consideration of usage limitations, preparation formulation and the like in the Japanese Pharmaceutical Excipients Directory. The amount of the fatty acid-based ionic liquid used is more preferably 4 times to 16 times based on a value of 1 for the amount used of the active ingredient in the form of pramipexole.

In addition, the content of the fatty acid-based ionic liquid is preferably about 4.5% by weight to 15% by weight in order to improve releasability of drug from the plaster. The added amount of fatty acid-based ionic liquid is preferably about 0.2 parts by weight to 0.7 parts by weight based on a value of 1 part by weight for the amount of plaster (total amount of elastomer and tackifier).

The "plaster" of the present invention refers to the adhesive layer of a transdermal patch, and in the case of comparing with the content of fatty acid-based ionic liquid as the amount of plaster in particular, represents the total amount of elastomer and tackifier. Although a known elastomer can be used for the elastomer, styrene-based thermoplastic elastomers, and particularly styrene-based block copolymers, are used preferably. More specifically, examples thereof include styrene-butadiene-styrene block copolymer, styrene-isoprene block copolymer, styrene-isoprene-styrene block copolymer (SIS), styrene-ethylene/butylene block copolymer, styrene-ethylene/butylene-styrene block copolymer, styrene-ethylene/propylene block copolymer, styrene-ethylene/propylene-styrene block copolymer, styrene-isobutylene block copolymer and styrene-isobutylene-styrene block copolymer. One type of these styrene-based block copolymers may be used alone or two or more types may be used in combination. A more preferable example is SIS. In addition, a tackifier commonly used in the field of adhesives can be used for the tackifier. Examples thereof include rosin-based resins, terpene resins, coumarone-indene resins, petroleum-based resins, terpene-phenol resins and alicyclic saturated hydrocarbon resins. A preferable example is terpene resin.

Furthermore, drug releasability becomes poor as the content of plaster (elastomer and tackifier) in terms of the amount added thereof increases, while adhesion to skin becomes poor if the amount thereof is excessively low. For this reason, the content of the plaster (elastomer and tackifier) is preferably about 10% by weight to 50% by weight and more preferably about 20% by weight to 45% by weight.

In addition, the composition of the plaster is preferably such that the amount of tackifier is preferably 1/4 parts by weight to 7/2 parts by weight based on 1 part by weight of elastomer, while the amount of tackifier is more preferably 1/3 parts by weight to 5/2 parts by weight. Moreover, the content of elastomer is preferably 8% by weight to 25% by weight.

Examples of the "divalent alcohol" of the present invention include propylene glycol, 1,3-butanediol, dipropylene glycol and polyethylene glycol. Preferable examples of divalent alcohols include propylene glycol, 1,3-butanediol and polyethylene glycol. One type of these divalent alcohols can be used alone or two or more types can be used in combination.

The "fatty acid ester" of the present invention is only required to be a known fatty acid ester used as a percutaneous absorption promoter, and examples thereof include diethyl sebacate, isopropyl myristate, diisopropyl adipate and propylene carbonate. Preferable examples include diethyl sebacate, isopropyl myristate and propylene carbonate. One type of these fatty acid esters can be used alone or two or more types can be used in combination. A combination of two types consisting of diethyl sebacate and isopropyl myristate can be used preferably.

The "tape preparation" of the present invention refers to a nonaqueous tape preparation that does not contain water as an essential ingredient. A general-purpose base can be used for the plaster of the transdermal patch of the present invention, and a base of an acrylic acid resin or a base obtained by adding an SIS resin, tackifier and softening agent and the like can be used. A preferable example of the base is a base containing SIS resin as an elastomer.

Examples of the "filler" of the present invention include inorganic, solid powdered reagents used in the plaster of transdermal patches such as silicic anhydride, zinc oxide, titanium oxide, calcium carbonate or kaolin, and organic, solid powdered reagents such as cornstarch, crystalline cellulose or stearic acid. Preferable examples of the filler of the present invention include the inorganic reagent, silicic anhydride, and the organic reagents of cornstarch and crystalline cellulose. More preferable examples include crystalline cellulose and silicic anhydride. The added amount of the filler is 1% by weight to 10% by weight and preferably 2% by weight to 8% by weight. Moreover, a combination of an inorganic, solid powdered reagent and an organic, solid powdered reagent can also be used for the filler.

Furthermore, a method similar to that used for known tape preparations can be used to prepare the transdermal patch of the present invention, and for example, the transdermal patch can be produced using a solvent coating method. An example of the aforementioned solvent coating method consists of preparing a plaster composition containing pramipexole and an ionic liquid, coating this directly onto a support and then drying. In addition, a method can also be employed in which the aforementioned plaster composition is temporarily coated onto release paper and dried followed by separating from the release paper and transferring and adhering to a support.

The aforementioned release paper is used for the purpose of protecting the adhesive layer, and release paper having one side treated with silicon can be used, examples of which include polyethylene-coated high-quality paper, polyolefin-based glassine paper, polyethylene terephthalate (PET) film and polypropylene film.

In the tape preparation of the present invention, additives such as an antioxidant, surfactant, thickener or pH adjuster may be further added within a range that does not impair the effects of the present invention. Commercially available reagents can be suitably used according to the purpose.

Examples of antioxidants include organic antioxidants such as BHT, propyl gallate or sodium ascorbate, and inorganic antioxidants such as sodium thiosulfate, sodium bisulfite, sodium sulfite or sodium pyrosulfite.

Examples of pH adjusters include organic acids such as citric acid, acetic acid or tartaric acid, and inorganic acids such as phosphoric acid or hydrochloric acid.

Moreover, a thickener such as Carbopol or an ultraviolet absorber and the like can also be added.

EXAMPLES

Although the following provides a more detailed explanation of the present invention based on examples and test examples, the present invention is not limited thereto.

Example 1

Selection of Preferable Ionic Liquid for Improving Percutaneous Absorption of Pramipexole Pramipexole dihydrochloride monohydrate was used for the active ingredient and each reagent was weighed out in the composite ratios indicated below (wt %). First, the pramipexole dihydrochloride monohydrate was dissolved in a mixed solution of fatty acid ionic liquid and organic solvent. Next, the pramipexole hydrochloride solution was added to a solution obtained by dissolving a plaster base consisting of SIS, liquid paraffin or tackifier and the like in hexane followed by stirring until uniform. This uniformly stirred viscous solution was then applied to a coater to prepare tape preparations.

Percutaneous absorption of the resulting tape preparations was evaluated based on the permeated amount of pramipexole 8 hours later using a Franz diffusion cell. The results are shown in Table 1.

| Test No. | K303V | K303U | K304W | K313U | K310G | K310H | K310I |
|---|---|---|---|---|---|---|---|
| Pramipexole 2HCl•H₂O | 1.0 | 1.0 | 1.0 | 1.0 | 1.0 | 1.0 | 1.0 |
| Ionic liquid: | | | | | | | |
| Isostearic acid (C18) | 3.9 | 2.1 | | | | | |
| Oleic acid (C18) | | 2.1 | 4.5 | 1.95 | | | |
| Palmitic acid (C16) | | | | 1.95 | 3.5 | 1.65 | |
| Myristic acid (C14) | | | | | | 1.65 | 3.10 |
| DIPA | 1.8 | 1.8 | 1.8 | 1.8 | 1.8 | 1.8 | 1.8 |
| Solvent: | | | | | | | |
| Propylene glycol | 13.0 | 13.0 | 13.0 | 13.0 | 13.0 | 13.0 | 13.0 |
| Diethyl sebacate | 7.0 | 7.0 | 7.0 | 7.0 | 7.0 | 7.0 | 7.0 |
| Isopropyl myristate | 3.0 | 3.0 | 3.0 | 3.0 | 3.0 | 3.0 | 3.0 |
| Plaster: | | | | | | | |
| SIS | 18.0 | 18.0 | 18.0 | 18.0 | 18.0 | 18.0 | 18.0 |
| Terpene resin | 6.0 | 6.0 | 6.0 | 6.0 | 6.0 | 6.0 | 6.0 |
| Liquid paraffin | 45.8 | 45.5 | 45.2 | 45.8 | 46.2 | 46.4 | 46.6 |
| Antioxidant: | | | | | | | |
| BHT | 0.5 | 0.5 | 0.5 | 0.5 | 0.5 | 0.5 | 0.5 |
| Total | 100.0 | 100.0 | 100.0 | 100.0 | 100.0 | 100.0 | 100.0 |
| Skin permeation amount: After 8 hr (μg/cm²) | 9.7 | 27.9 | 39.0 | 18.3 | 12.1 | 22.3 | 35.4 |

Figure 2:
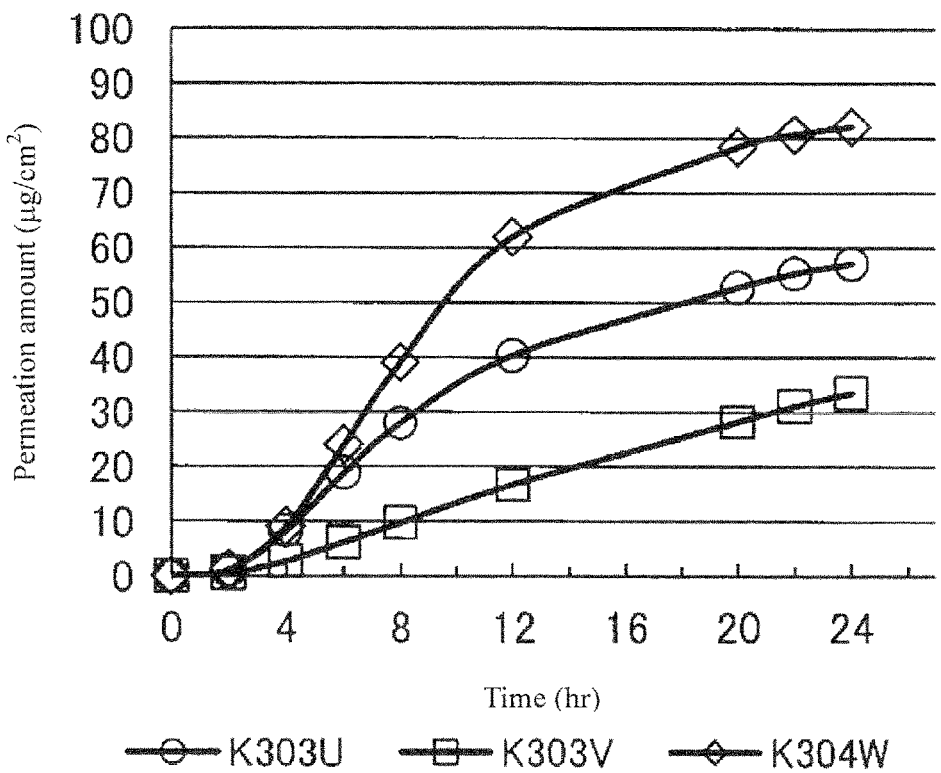
FIG. 2 is a graph representing cumulative drug permeation amounts at various times of three samples of test nos. K303U, K303V and K304W.

Based on the aforementioned Table 1 and FIG. 2, the fatty acid-based ionic liquid clearly demonstrated an effect of promoting percutaneous absorption of pramipexole. First, when evaluated in terms of the amount of pramipexole that permeated the skin, the percutaneous absorption promoting effects of the oleic acid-based ionic liquid (diisopropanolamine salt) and the myristic acid-based ionic liquid (diisopropanolamine salt) were determined to be large. Mixed ionic liquids demonstrated additive percutaneous adsorption promoting effects as indicated by test nos. K303U, K313U and K310H in Table 1.

In addition, the amount of pramipexole that permeated the skin was determined to increase as the amount of ionic liquid used increased.

TABLE 2

| | Test No. | | | | |
|---|---|---|---|---|---|
| | K303V | K303U | K313S | K312L | K313T |
| Pramipexole 2HCl•H₂O | 1.0 | 1.0 | 1.0 | 1.0 | 1.0 |
| Ionic liquid: | | | | | |
| Isostearic acid (C18) | 3.9 | 2.1 | 1.85 | 1.70 | |
| Oleic acid (C18) | | 2.1 | | | 1.85 |
| Palmitic acid (C16) | | | 1.85 | | |
| Myristic acid (C14) | | | | 1.70 | 1.85 |
| DIPA | 1.8 | 1.8 | 1.8 | 1.8 | 1.8 |
| Solvent: | | | | | |
| Propylene glycol | 13.0 | 13.0 | 13.0 | 13.0 | 13.0 |
| Diethyl sebacate | 7.0 | 7.0 | 7.0 | 7.0 | 7.0 |
| Isopropyl myristate | 3.0 | 3.0 | 3.0 | 3.0 | 3.0 |
| Plaster: | | | | | |
| SIS | 18.0 | 18.0 | 18.0 | 18.0 | 18.0 |
| Terpene resin | 6.0 | 6.0 | 6.0 | 6.0 | 6.0 |
| Liquid paraffin | 45.8 | 45.5 | 46.00 | 46.3 | 46.0 |
| Antioxidant: | | | | | |
| BHT | 0.5 | 0.5 | 0.5 | 0.5 | 0.5 |
| Total | 100.0 | 100.0 | 100.0 | 100.0 | 100.0 |
| Skin permeation amount: After 8 hr (μg/cm²) | 9.7 | 27.9 | 37.0 | 32.1 | 28.1 |

As is shown in Table 2 above, when various combinations of mixed ionic liquids were used that consisted mainly of oleic acid and myristic acid which demonstrate potent percutaneous absorption promoting effects, permeation amounts of about 30 μg/cm² to 35 μg/cm² were determined to be obtained.

Example 2

Percutaneous Absorption Promoting Effect of Alkanolamine in Ionic Liquid

The type of alkanolamine in the fatty acid-based ionic liquid was changed while keeping the fatty acid composition the same followed by confirming the effect thereof. Reagents were weighed out as shown in the following Table 2 (wt %) and tape preparations were produced in the same manner as Example 1.

Percutaneous absorption of the resulting tape preparations was evaluated based on the permeated amount of pramipexole 8 hours later using a Franz diffusion cell. The results are shown in the following Table 3.

TABLE 3

|  | Test No. | | |
| --- | --- | --- | --- |
|  | K303U | K304X | K312K |
| Pramipexole 2HCl•$H_2O$ | 1.0 | 1.0 | 1.0 |
| Ionic liquid: | | | |
| Isostearic acid (C18) | 2.1 | 2.1 | 2.1 |
| Oleic acid (C18) | 2.1 | 2.1 | 2.1 |
| DIPA | 1.8 |  | 0.95 |
| TEA |  | 2.0 | 0.95 |
| Solvent: | | | |
| Propylene glycol | 13.0 | 13.0 | 13.0 |
| Diethyl sebacate | 7.0 | 7.0 | 7.0 |
| Isopropyl myristate | 3.0 | 3.0 | 3.0 |
| Plaster: | | | |
| SIS | 18.0 | 18.0 | 18.0 |
| Terpene resin | 6.0 | 6.0 | 6.0 |
| Liquid paraffin | 45.5 | 45.3 | 45.4 |
| Antioxidant: | | | |
| BHT | 0.5 | 0.5 | 0.5 |
| Total | 100.0 | 100.0 | 100.0 |
| Skin permeation amount: After 8 hr ($\mu g/cm^2$) | 27.9 | 13.5 | 29.3 |

As shown in Table 3, preparation of a fatty acid-based ionic liquid using a strongly basic secondary alkanolamine in the form of diisopropylamine was determined to facilitate formation of an ion complex with pramipexole in the solution and improve percutaneous absorption to a greater degree than when using a tertiary alkanolamine in the form of triethanolamine.

An ionic liquid having the composition indicated above was prepared using a mixture of triethanolamine and diisopropanolamine (weight ratio: 1:1) for the alkanolamine followed by evaluating the percutaneous absorption improving effect thereof. As a result, the strongly basic diisopropanolamine (pH 8.9) was determined to impart a dominant effect on percutaneous absorption improving effect to a greater degree than triethanolamine (pH 7.8).

Example 3

Effect of Filler

The fatty acid-based ionic liquid fulfills the role of a surfactant in that it dissolves pramipexole together with the organic solvent and causes the dissolved pramipexole solution to be dispersed in the plaster. Namely, the fatty acid-based ionic liquid forms micelles of an ionic liquid containing pramipexole that are dispersed in the plaster. However, since fluidity in the plaster is poor and mass transfer within the plaster is inhibited, it was difficult for the micelles to be released from the plaster. As a result, the drug easily remains within the transdermal patch and percutaneous absorption tended to be the rate-determining factor of release from the plaster.

As a result of previous research, the addition of a filler (powdered solid that is insoluble in the organic solvent, ionic liquid and plaster) to the plaster was determined to result in the formation of voids due to association among the filler, and the voids that formed were determined to be able be used as drug release channels to promote mass transfer within the plaster.

In the present invention as well, an attempt was made to facilitate release onto the surface of the plaster by allowing micelles of the ionic liquid dispersed within the plaster to be conveyed through the voids formed by the filler. Consequently, a study was conducted as to what type of filler is appropriate. Namely, crystalline cellulose (Ceolus) was used as an organic filler and silicic anhydride was used as an inorganic filler. Each reagent was weighed out in the compositions (wt %) shown in the following Table 4 and tape preparations were produced in the same manner as Example 1.

Percutaneous absorption (skin permeation) of the resulting tape preparations was evaluated in terms of the amount of pramipexole that permeated the skin 8 hours later using a Franz diffusion cell. The results are shown in the following Table 4.

TABLE 4

|  | Test No. | | | |
| --- | --- | --- | --- | --- |
|  | K300R | K301S | K301T | K312J |
| Pramipexole 2HCl•$H_2O$ | 1.0 | 1.0 | 1.0 | 1.0 |
| Ionic liquid: | | | | |
| Isostearic acid (C18) | 1.5 | 1.5 | 1.5 | 1.5 |
| Oleic acid (C18) | 0.4 | 0.4 | 0.4 | 0.4 |
| Palmitic acid (C16) | 1.5 | 1.5 | 1.5 | 1.5 |
| Myristic acid (C14) | 0.3 | 0.3 | 0.3 | 0.3 |
| DIPA | 1.8 | 1.8 | 1.8 | 1.8 |
| Solvent: | | | | |
| Propylene glycol | 13.0 | 13.0 | 13.0 | 13.0 |
| Diethyl sebacate | 7.0 | 7.0 | 7.0 | 7.0 |
| Isopropyl myristate | 3.0 | 3.0 | 3.0 | 3.0 |
| Plaster: | | | | |
| SIS | 18.0 | 18.0 | 18.0 | 18.0 |
| Terpene resin | 6.0 | 6.0 | 6.0 | 6.0 |
| Liquid paraffin | 46.0 | 43.0 | 43.0 | 43.0 |
| Filler: | | | | |
| Light silicic anhydride |  | 3.0 |  | 1.5 |
| Ceolus |  |  | 3.0 | 1.5 |
| Antioxidant: | | | | |
| BHT | 0.5 | 0.5 | 0.5 | 0.5 |
| Total | 100.0 | 100.0 | 100.0 | 100.0 |
| Skin permeation amount: After 8 hr ($\mu g/cm^2$) | 23.8 | 24.4 | 33.8 | 27.3 |

As shown in Table 4 above, the amount of pramipexole that permeated the skin was higher in the case of using an organic filler in the form of crystalline cellulose than in the case of using an inorganic filler in the form of silicic anhydride. Since the compositions other than the type of organic filler are the same, the difference in the skin permeation amount is affected by the degree of the release rate of drug from the plaster. Namely, the use of an organic filler is thought to facilitate release of pramipexole. This is thought to be the result of the use of an organic filler facilitating the formation of voids (release channels) suitable for the release of ionic liquid containing pramipexole.

In this manner, as a result of having formed suitable voids (release channels) by using an organic filler, the skin permeation amount was indicated to increase by about 1.5 times in comparison with the case of using an inorganic filler. Namely, the use of an organic filler results in a roughly 1.5-fold increase in releasability of pramipexole from the plaster.

Moreover, in the case of having used an inorganic filler in the form of silicic anhydride, the resulting skin permeation amount was only demonstrated to be similar to that of test no. K300R to which a filler was not added. This is thought to be because, due to the high acidity in the case of using silicic anhydride, the pramipexole that forms an ion complex is easily trapped by the silicic anhydride in the same manner in which ion complexes and salts are trapped by a silica gel column, thereby inhibiting releasability.

Therefore, a tape preparation was produced having a composition in which the weight ratio of crystalline cellulose to silicic anhydride was 1:1 followed by evaluating the skin permeation amount of pramipexole. As a result, as indicated by test no. K312J, skin permeation amounts were demonstrated that approached the average value of nos. K301S and K301T. On the basis thereof, the effect of adding filler was determined to be an additive effect.

Example 4

Preferable Range of Added Amount of Plaster (SIS and Terpene Resin) in Tape Preparation Since plaster (SIS and terpene resin) has poor fluidity, mass transfer of pramipexole contained in the ionic liquid dispersed in the plaster is difficult. For this reason, when the amount of plaster is increased and the content of liquid paraffin is decreased, the plaster becomes hard resulting in a further decrease in mass transfer within the plaster. Namely, since the amount of pramipexole released from the plaster decreases if the amount of plaster is increased, the amount of pramipexole that permeates the skin also decreases. Therefore, in order to evaluate the effect of the amount of plaster on skin permeation, each reagent was weighed out in the compositions (wt %) shown in Table 5 to produce tape preparations based on Example 1.

Percutaneous absorption (skin permeation) of the resulting tape preparations was evaluated in terms of the amount of pramipexole that permeated the skin 8 hours later using a Franz diffusion cell. The results are shown in the following Table 5.

TABLE 5

| | Test No. | | | |
|---|---|---|---|---|
| | K308E | K304Z | K305B | K308F |
| Pramipexole 2HCl•$H_2O$ | 1.0 | 1.0 | 1.0 | 1.0 |
| Ionic liquid: | | | | |
| Isostearic acid (C18) | 2.1 | 2.1 | 2.1 | 2.1 |
| Oleic acid (C18) | 2.1 | 2.1 | 2.1 | 2.1 |
| DIPA | 1.8 | 1.8 | 1.8 | 1.8 |
| Solvent: | | | | |
| Propylene glycol | 13.0 | 13.0 | 13.0 | 13.0 |
| Diethyl sebacate | 7.0 | 7.0 | 7.0 | 7.0 |
| Isopropyl myristate | 3.0 | 3.0 | 3.0 | 3.0 |
| Plaster: | | | | |
| SIS | 21.0 | 18.0 | 15.0 | 12.0 |
| Terpene resin | 21.0 | 18.0 | 15.0 | 12.0 |
| Liquid paraffin | 27.5 | 33.5 | 39.5 | 45.5 |
| Antioxidant: | | | | |
| BHT | 0.5 | 0.5 | 0.5 | 0.5 |
| Total | 100.0 | 100.0 | 100.0 | 100.0 |
| Skin permeation amount: After 8 hr ($\mu g/cm^2$) | 16.4 | 22.1 | 35.6 | 39.1 |

As shown in Table 5 above, the amount of pramipexole that permeated the skin increased as the amounts of SIS and tackifier (terpene resin) of the plaster decreased and the amount of liquid paraffin increased. Namely, pramipexole was more easily released from the plaster. This indicates that mass transfer within the plaster occurs more easily if the amount of SIS and tackifier (terpene resin) of the plaster decreases and the amount of liquid paraffin increases. On the other hand, adhesion to the skin decreases if the amount of SIS and tackifier (terpene resin) of the plaster decreases. For this reason, a certain amount of SIS and tackifier (terpene resin) is required. Based on Table 5 above, both adhesiveness and releasability of pramipexole from the plaster were indicated to be favorable if the weight composition of SIS and terpene resin (amount of plaster) is 20% by weight to 30% by weight.

Example 5

Preferable Composition Range of Plaster (SIS and Terpene Resin) in Transdermal Patch Skin permeation (percutaneous absorption) of a drug is determined by two factors (rate-determining factor of skin absorption and rate-determining factor of releasability from plaster). Due to the effects of an ionic liquid or percutaneous absorption promoter and the like, if the skin absorption of a drug is high, releasability of the drug from the plaster becomes the rate-determining factor and is governed by skin permeation of the drug. On the other hand, if skin absorption of a drug is poor, that absorption becomes the rate-determining factor and this is governed by the skin permeation amount of the drug.

As indicated in Example 4, since mass transfer within the plaster is difficult in the case of a high content of plaster (SIS and terpene resin), it is difficult for pramipexole dispersed in the plaster to be released from the plaster. Namely, since the rate-determining factor of releasability from the plaster becomes the controlling factor when the amount of plaster increases, the percutaneous absorption promoting effect of the ionic liquid of the present invention cannot be evaluated.

Therefore, an evaluation was conducted as to the manner in which releasability of pramipexole from the plaster is affected by the composition of the plaster (composition of elastomer and tackifier). Consequently, each reagent was weighed out in the compositions (wt %) shown in the following Table 6 to produce tape preparations based on Example 1.

Percutaneous absorption (skin permeation) of the resulting tape preparations was evaluated in terms of the amount of pramipexole that permeated the skin 8 hours later using a Franz diffusion cell. The results are shown in the following Table 6.

TABLE 6

| | Test No. | | | |
|---|---|---|---|---|
| | K303U | K304Y | K304Z | K305A |
| Pramipexole 2HCl•H$_2$O | 1.0 | 1.0 | 1.0 | 1.0 |
| Ionic liquid: | | | | |
| Isostearic acid (C18) | 2.1 | 2.1 | 2.1 | 2.1 |
| Oleic acid (C18) | 2.1 | 2.1 | 2.1 | 2.1 |
| DIPA | 1.8 | 1.8 | 1.8 | 1.8 |
| Solvent: | | | | |
| Propylene glycol | 13.0 | 13.0 | 13.0 | 13.0 |
| Diethyl sebacate | 7.0 | 7.0 | 7.0 | 7.0 |
| Isopropyl myristate | 3.0 | 3.0 | 3.0 | 3.0 |
| Plaster: | | | | |
| SIS | 18.0 | 18.0 | 18.0 | 18.0 |
| Terpene resin | 6.0 | 12.0 | 18.0 | 24.0 |
| Polybutene | | | | |
| Liquid paraffin | 45.5 | 39.5 | 33.5 | 27.5 |
| Antioxidant: | | | | |
| BHT | 0.5 | 0.5 | 0.5 | 0.5 |
| Total | 100.0 | 100.0 | 100.0 | 100.0 |
| Skin permeation amount: After 8 hr (μg/cm$^2$) | 27.9 | 29.0 | 22.1 | 21.0 |

As shown in Table 6 above, even if the amount of SIS elastomer remained constant, mass transfer of the drug in the plaster is gradually inhibited if the amount of terpene resin tackifier increases and the amount of liquid paraffin decreases. As a result, since release of pramipexole from the plaster is inhibited, the skin permeation amount decreases and release of pramipexole from the plaster becomes the rate-determining factor. Thus, in order to avoid the release of pramipexole from the plaster from becoming the rate-determining factor, it was indicated based on the results of K303U and K304 in the aforementioned Table 6 that the plaster composition should be such that the amount of terpene resin is within the range of 1/3 parts by weight to 2/3 parts by weight based on a value of 1 part by weight of SIS. It was clearly determined that if the amount terpene resin is within this range, the release of pramipexole from the plaster does not become the rate-determining factor of the skin permeation amount of pramipexole.

Moreover, compositions of tape preparations were able to be arranged in the manner of Table 7 below with reference to the results of Example 4 in order to evaluate the proper range of the elastomer in the form of SIS.

TABLE 7

| | Test No. | | | |
|---|---|---|---|---|
| | K304Y | K305B | K303U | K308F |
| Pramipexole 2HCl•H$_2$O | 1.0 | 1.0 | 1.0 | 1.0 |
| Ionic liquid: | | | | |
| Isostearic acid (C18) | 2.1 | 2.1 | 2.1 | 2.1 |
| Oleic acid (C18) | 2.1 | 2.1 | 2.1 | 2.1 |
| DIPA | 1.8 | 1.8 | 1.8 | 1.8 |
| Solvent: | | | | |
| Propylene glycol | 13.0 | 13.0 | 13.0 | 13.0 |
| Diethyl sebacate | 7.0 | 7.0 | 7.0 | 7.0 |
| Isopropyl myristate | 3.0 | 3.0 | 3.0 | 3.0 |
| Plaster: | | | | |
| SIS | 18.0 | 15.0 | 18.0 | 12.0 |
| Terpene resin | 12.0 | 15.0 | 6.0 | 12.0 |
| (SIS + resin) | 30.0 | 30.0 | 24.0 | 24.0 |
| Liquid paraffin | 39.5 | 39.5 | 45.5 | 45.5 |
| Antioxidant: | | | | |
| BHT | 0.5 | 0.5 | 0.5 | 0.5 |
| Total | 100.0 | 100.0 | 100.0 | 100.0 |
| Skin permeation amount: After 8 hr (μg/cm$^2$) | 29.0 | 35.6 | 27.9 | 39.1 |

As shown in Table 7 above, in the case the total amounts of elastomer (SIS) and tackifier (terpene resin) in the plaster are the same, comparisons among test nos. K304Y and K305B and between test nos. K303U and K308F were determined to indicate that a smaller amount of elastomer results in better skin permeation. Namely, a smaller amount of elastomer was determined to result in better drug releasability. Based on the results of previous studies of percutaneous absorption, an elastomer content of 8% by weight to 15% by weight was determined to facilitate avoidance of the release from the plaster becoming the rate-determining factor.

Therefore, in order to verify results obtained thus far, the correlation between the total amount of elastomer and tackifier in the plaster and skin permeation amount was summarized in the following Table 8.

TABLE 8

| Test No. | K308E | K304Y | K305B | K308D | K303U | K308F | K308C |
|---|---|---|---|---|---|---|---|
| Pramipexole 2HCl•H$_2$O | 1.0 | 1.0 | 1.0 | 1.0 | 1.0 | 1.0 | 1.0 |
| Ionic liquid: | | | | | | | |
| Isostearic acid (C18) | 2.1 | 2.1 | 2.1 | 2.1 | 2.1 | 2.1 | 2.1 |
| Oleic acid (C18) | 2.1 | 2.1 | 2.1 | 2.1 | 2.1 | 2.1 | 2.1 |
| DIPA | 1.8 | 1.8 | 1.8 | 1.8 | 1.8 | 1.8 | 1.8 |

TABLE 8-continued

| Test No. | K308E | K304Y | K305B | K308D | K303U | K308F | K308C |
|---|---|---|---|---|---|---|---|
| Solvent: | | | | | | | |
| Propylene glycol | 13.0 | 13.0 | 13.0 | 13.0 | 13.0 | 13.0 | 13.0 |
| Diethyl sebacate | 7.0 | 7.0 | 7.0 | 7.0 | 7.0 | 7.0 | 7.0 |
| Isopropyl myristate | 3.0 | 3.0 | 3.0 | 3.0 | 3.0 | 3.0 | 3.0 |
| Plaster: | | | | | | | |
| SIS | 21.0 | 18.0 | 15.0 | 21.0 | 18.0 | 12.0 | 15.0 |
| Terpene resin | 21.0 | 12.0 | 15.0 | 7.0 | 6.0 | 12.0 | 5.0 |
| (SIS + resin) | 42.0 | 30.0 | 30.0 | 28.0 | 24.0 | 24.0 | 20.0 |
| Liquid paraffin | 27.5 | 39.5 | 39.5 | 41.5 | 45.5 | 45.5 | 49.5 |
| Antioxidant: | | | | | | | |
| BHT | 0.5 | 0.5 | 0.5 | 0.5 | 0.5 | 0.5 | 0.5 |
| Total | 100.0 | 100.0 | 100.0 | 100.0 | 100.0 | 100.0 | 100.0 |
| Skin permeation amount: After 8 hr ($\mu g/cm^2$) | 16.4 | 29.0 | 35.6 | 29.6 | 27.9 | 39.1 | 31.6 |

As shown in Table 8 above, even if the amount of liquid paraffin and total amount of the plaster remain constant (69.5% by weight), if the amount of the plaster (total amount of elastomer and tackifier) exceeds 30% by weight and the plaster composition is such that the terpene resin exceeds 2/3 parts by weight based on 1 part by weight of SIS, skin permeation decreases and the contribution of the rate-determining factor of the release of drug increases. In addition, even if the total amounts of elastomer and tackifier are the same, a smaller amount of elastomer was determined to impart better skin permeation. Namely, a lower elastomer content was indicated to result in better drug releasability and make it more difficult for the release of drug to be the rate-determining factor.

On the basis of the above, in order to avoid the release of drug from becoming the rate-determining factor, the total amount of elastomer and tackifier in the plaster was indicated to preferably be 30% by weight or less, the content of elastomer preferably 8% by weight to 15% by weight, and the amount of tackifier preferably within the range of 1/3 to 2/3 of the elastomer.

Example 6

Preferable Added Amount of Ionic Liquid in Tape Preparation

As was previously described in Example 5, the amount of a drug that permeates the skin (percutaneous absorption) is determined by two factors (rate-determining factor of skin absorption and rate-determining factor of releasability from plaster). In the case of a high content of ionic liquid and solvent, the plaster softens making it easier for pramipexole to be released from the plaster. Namely, the rate-determining factor of skin absorption becomes the controlling factor when the amount of solvent is constant while the amount of ionic liquid increases. Conversely, the rate-determining factor of the release of pramipexole becomes the controlling factor when the amount of ionic liquid decreases. Therefore, the preferable range for the amount of ionic liquid added over which the rate-determining factor of skin absorption becomes the controlling factor was evaluated by evaluating the correlation between the added amount of ionic liquid and the amount of pramipexole that permeates the skin. Therefore, each reagent was weighed out in the composite ratios (wt %) shown in the following Table 9 and tape preparations were produced based on Example 1.

Percutaneous absorption (skin permeation) of the resulting tape preparation was evaluated based on the permeated amount of pramipexole 8 hours later using a Franz diffusion cell. The results are shown in the following Table 9.

TABLE 9

| Test No. | K314V | K314W | K315Y | K303U | K315Z | K314X |
|---|---|---|---|---|---|---|
| Pramipexole 2HCl·H$_2$O | 1.0 | 1.0 | 1.0 | 1.0 | 1.0 | 1.0 |
| Ionic liquid: | | | | | | |
| Isostearic acid (C18) | 0.25 | 0.50 | 1.05 | 2.1 | 4.15 | 5.15 |
| Oleic acid (C18) | 0.25 | 0.50 | 1.05 | 2.1 | 4.15 | 5.15 |
| DIPA | 0.22 | 0.45 | 0.9 | 1.8 | 3.6 | 4.50 |
| Solvent: | | | | | | |
| Propylene glycol | 13.0 | 13.0 | 13.0 | 13.0 | 13.0 | 13.0 |
| Diethyl sebacate | 7.0 | 7.0 | 7.0 | 7.0 | 7.0 | 7.0 |
| Isopropyl myristate | 3.0 | 3.0 | 3.0 | 3.0 | 3.0 | 3.0 |
| Plaster: | | | | | | |
| SIS | 18.0 | 18.0 | 18.0 | 18.0 | 18.0 | 18.0 |
| Terpene resin | 6.0 | 6.0 | 6.0 | 6.0 | 6.0 | 6.0 |
| Liquid paraffin | 50.78 | 50.05 | 48.5 | 45.5 | 39.6 | 36.7 |
| Antioxidant: | | | | | | |
| BHT | 0.5 | 0.5 | 0.5 | 0.5 | 0.5 | 0.5 |
| Total | 100.0 | 100.0 | 100.0 | 100.0 | 100.0 | 100.0 |
| Skin permeation amount: After 8 hr ($\mu g/cm^2$) | 4.4 | 2.7 | 7.2 | 27.9 | 35.7 | 42.4 |

As indicated by test nos. K314V to K315Y in Table 9 above, when the amount of ionic liquid decreases, skin permeation amount decreases and release from the plaster was indicated to be the rate-determining factor. For this reason, it was determined that, if the content of ionic liquid in the tape preparation is not about 5% by weight or more, release of drug easily becomes the rate-determining factor. In addition, it was also determined that, if the content of ionic liquid exceeds about 12% by weight, the effect of release from the plaster being the rate-determining factor is diminished, while the rate-determining factor of skin absorption becomes the controlling factor. If the amount of plaster (total amount of SIS and terpene resin) is made to be 1 part by weight, then the amount of ionic liquid is required to be about 0.2 parts by weight or more, and an amount of about 0.7 parts by weight is considered to be adequate.

Example 7

Evaluation of Rate-Determining Factor of Skin Absorption and Examination of Preparation Formulation on the Basis Thereof In the aforementioned Examples 3 to 6, an examination of preparation formulation was made by evaluating releasability of pramipexole from the plaster. Namely, preparation formulation was examined while focusing on the rate-determining factor of release in transdermal patches. Consequently, examination of preparation formulation while focusing on the rate-determining factor of skin absorption in transdermal patches was not adequate. In the background thereof, there is the question of whether the use of skin adsorption for rate-determining factor or drug release for the rate-determining factor can be adequately distinguished with respect to the previous use of skin permeation amount as an evaluation index.

Therefore, the inventors of the present invention decided to make the plaster composition and the proportion of the involvement of drug releasability constant and further change the evaluation index in order to use skin permeation rate per unit time (in the 4th hour after application) instead of skin permeation amount for the evaluation index. As a result, skin absorption was able to be evaluated more accurately. Namely, it was thought that it would be possible to suitably examine preparation formulation in order to optimize skin absorption.

Therefore, the skin permeation rate of pramipexole was calculated from the data obtained in Example 1 and those results are shown in the following Tables 10 and 11.

TABLE 10

| Test No. | K303V | K303U | K304W | K313U | K310G | K310H | K310I |
|---|---|---|---|---|---|---|---|
| Pramipexole 2HCl·H$_2$O | 1.0 | 1.0 | 1.0 | 1.0 | 1.0 | 1.0 | 1.0 |
| Ionic liquid: | | | | | | | |
| Isostearic acid (C18) | 3.9 | 2.1 | | | | | |
| Oleic acid (C18) | | 2.1 | 4.5 | 1.95 | | | |
| Palmitic acid (C16) | | | | 1.95 | 3.5 | 1.65 | |
| Myristic acid (C14) | | | | | | 1.65 | 3.10 |
| DIPA | 1.8 | 1.8 | 1.8 | 1.8 | 1.8 | 1.8 | 1.8 |
| Solvent: | | | | | | | |
| Propylene glycol | 13.0 | 13.0 | 13.0 | 13.0 | 13.0 | 13.0 | 13.0 |
| Diethyl sebacate | 7.0 | 7.0 | 7.0 | 7.0 | 7.0 | 7.0 | 7.0 |
| Isopropyl myristate | 3.0 | 3.0 | 3.0 | 3.0 | 3.0 | 3.0 | 3.0 |
| Plaster: | | | | | | | |
| SIS | 18.0 | 18.0 | 18.0 | 18.0 | 18.0 | 18.0 | 18.0 |
| Terpene resin | 6.0 | 6.0 | 6.0 | 6.0 | 6.0 | 6.0 | 6.0 |
| Liquid paraffin | 45.8 | 45.5 | 45.2 | 45.8 | 46.2 | 46.4 | 46.6 |
| Antioxidant: | | | | | | | |
| BHT | 0.5 | 0.5 | 0.5 | 0.5 | 0.5 | 0.5 | 0.5 |
| Total | 100.0 | 100.0 | 100.0 | 100.0 | 100.0 | 100.0 | 100.0 |
| Skin permeation rate: After 4 hr (μg/cm$^2$·hr) | 1.1 | 3.6 | 4.0 | 1.8 | 0.9 | 2.2 | 4.3 |

TABLE 11

| | Test No. | | | | |
|---|---|---|---|---|---|
| | K303V | K303U | K313S | K312L | K313T |
| Pramipexole 2HCl•H₂O | 1.0 | 1.0 | 1.0 | 1.0 | 1.0 |
| Ionic liquid: | | | | | |
| Isostearic acid (C18) | 3.9 | 2.1 | 1.85 | 1.70 | |
| Oleic acid (C18) | | 2.1 | | | 1.85 |
| Palmitic acid (C16) | | | 1.85 | | |
| Myristic acid (C14) | | | | 1.70 | 1.85 |
| DIPA | 1.8 | 1.8 | 1.8 | 1.8 | 1.8 |
| Solvent: | | | | | |
| Propylene glycol | 13.0 | 13.0 | 13.0 | 13.0 | 13.0 |
| Diethyl sebacate | 7.0 | 7.0 | 7.0 | 7.0 | 7.0 |
| Isopropyl myristate | 3.0 | 3.0 | 3.0 | 3.0 | 3.0 |
| Plaster: | | | | | |
| SIS | 18.0 | 18.0 | 18.0 | 18.0 | 18.0 |
| Terpene resin | 6.0 | 6.0 | 6.0 | 6.0 | 6.0 |
| Liquid paraffin | 45.8 | 45.5 | 46.00 | 46.3 | 46.0 |
| Antioxidant: | | | | | |
| BHT | 0.5 | 0.5 | 0.5 | 0.5 | 0.5 |
| Total | 100.0 | 100.0 | 100.0 | 100.0 | 100.0 |
| Skin permeation rate: After 4 hr (μg/cm² · hr) | 1.1 | 3.6 | 5.4 | 4.8 | 2.9 |

As shown in Tables 10 and 11 above and FIG. 1, when evaluated by using skin permeation rate in the 4th hour after application as an index, the contributions of oleic acid and myristic acid were determined to be large.

In addition, when considering that skin permeation rate is subjected to the effects of diffusion rate in the skin, the results of the aforementioned Tables 10 and 11 are thought to reflect the skin absorption promoting effect of the ionic liquid together with the diffusion promoting effect in the skin.

Furthermore, a comparison with the results of Table 1 of Example 1 is summarized in the following Table 12.

trends. For example, as indicated in FIGS. 1 and 2 and FIGS. 3 and 4, a positive correlation is demonstrated between skin permeation rate and skin permeation amount. Thus, if skin permeation rate and skin permeation amount are used as indices, nearly additive percutaneous absorption promoting effects were determined to be demonstrated in the case of a mixed ionic liquid.

However, when using a single ionic liquid, in the case of a mixed ionic liquid of isostearic acid and palmitic acid, for which percutaneous absorption promoting effects are not high, skin permeation amount and skin permeation rate were demonstrated to be synergistic and not additive.

Figure 3:
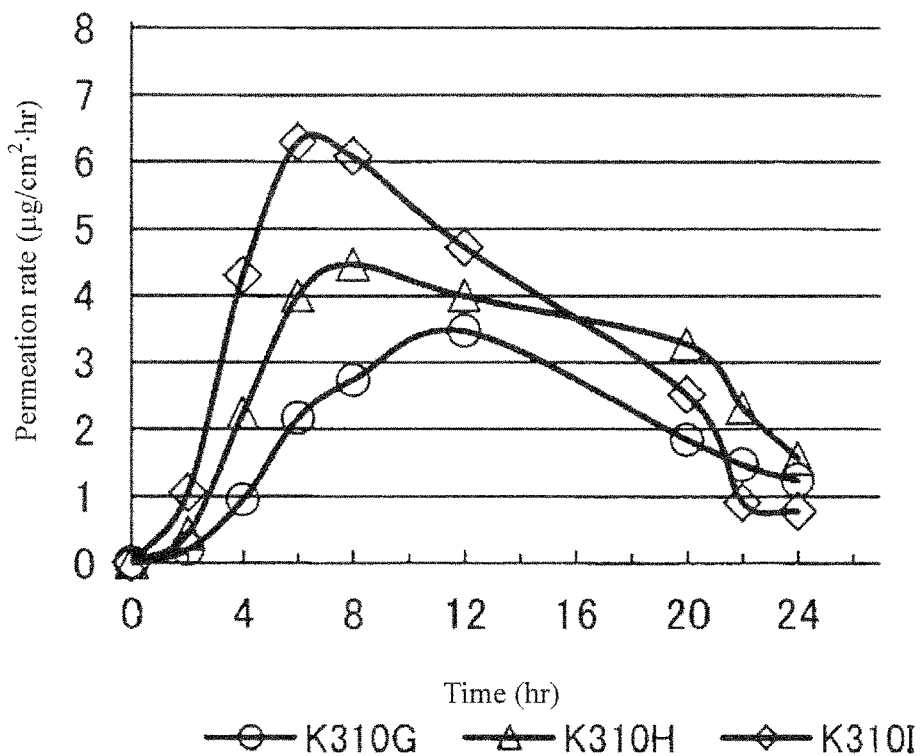
FIG. 3 is a graph representing changes in skin absorption rates at various times of three samples of test nos. K310G, K310H and K310I.
Figure 4:
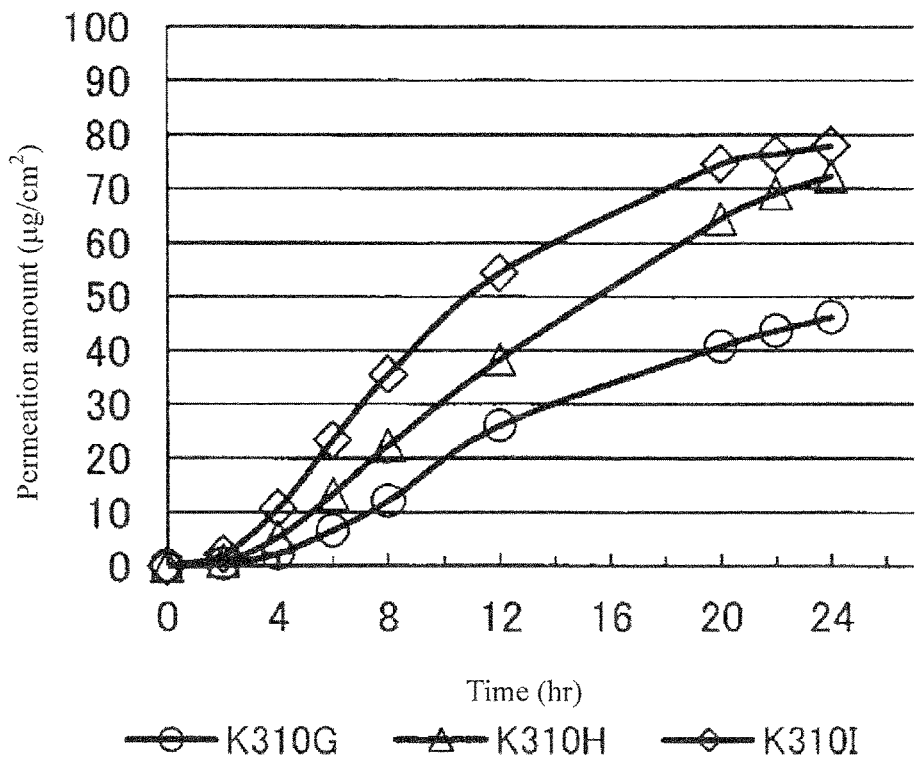
FIG. 4 is a graph representing changes in cumulative skin permeation amounts at various times of three samples of test nos. K310G, K310H and K310I.

In addition, according to FIGS. 1 and 3, skin permeation rate in the 4th hour after application occurred prior to skin permeation rate attaining its maximum value, and this measurement time is thought to be a time at which it is difficult for the effect of releasability of drug from the plaster to appear. Namely, skin permeation rate in the 4th hour after application is thought to mainly reflect the skin absorption effect of the ionic liquid. On the other hand, skin permeation amount at 8 hours after application is thought to be an index that represents not only the skin absorption effect of the ionic liquid, but also the overall percutaneous absorption of the tape preparation that encompasses both the diffusion rate of drug in the skin as well as the release rate of drug from the plaster.

In this manner, by combining the use of skin permeation rate and skin permeation amount as evaluation indices, evaluations can be carried out while distinguishing between whether the percutaneous absorption effect of the fatty acid-based ionic liquid reflects the rate-determining factor of skin absorption or reflects the rate-determining factor of release from the plaster. As a result, this makes it possible to select a more suitable ionic liquid or more suitable mixed ionic liquid. Namely, it was determined that, with respect to

TABLE 12

| Test No. | K303V | K303U | K304W | K313U | K310G | K310H | K310I | K313S | K312L | K313T |
|---|---|---|---|---|---|---|---|---|---|---|
| Pramipexole 2HCl•H₂O | 1.0 | 1.0 | 1.0 | 1.0 | 1.0 | 1.0 | 1.0 | 1.0 | 1.0 | 1.0 |
| Ionic liquid: | | | | | | | | | | |
| Isostearic acid (C18) | 3.9 | 2.1 | | | | | | 1.85 | 1.70 | |
| Oleic acid (C18) | | 2.1 | 4.5 | 1.95 | | | | | | 1.85 |
| Palmitic acid (C16) | | | | 1.95 | 3.5 | 1.65 | | 1.85 | | |
| Myristic acid (C14) | | | | | | 1.65 | 3.10 | | 1.70 | 1.85 |
| DIPA | 1.8 | 1.8 | 1.8 | 1.8 | 1.8 | 1.8 | 1.8 | 1.8 | 1.8 | 1.8 |
| Skin permeation rate: After 4 hr (μg/cm² · hr) | 1.1 | 3.6 | 4.0 | 1.8 | 0.9 | 2.2 | 4.3 | 5.4 | 4.8 | 2.9 |
| Skin permeation amount: After 8 hr (μg/cm²) | 9.7 | 27.9 | 39.0 | 18.3 | 12.1 | 22.3 | 35.4 | 37.0 | 32.1 | 28.1 |

As indicated in Table 12 above, there is a high degree of correlation between skin permeation rate in the 4th hour after application and skin permeation amount 8 hours after application, and both parameters demonstrated similar pramipexole, it is preferable to use an oleic acid-based ionic liquid and myristic acid-based ionic liquid as basic percutaneous absorption promoters, or use a mixed ionic liquid consisting of these ionic liquids and an isostearic acid-based ionic liquid and the like.

Example 8

Effect of Alkanolamine on Skin Permeation Rate

An attempt was made to verify the use of skin permeation rate in Example 7 as an index for evaluating the percutaneous absorption promoting effect of a fatty acid-based ionic liquid. Therefore, in order to evaluate the effect of alkanolamine on skin permeation rate, skin permeation rate was calculated from the data of Example 2, and those results are summarized in the following Table 13 along with the results of Table 3.

TABLE 13

|  | Test No. | | |
| --- | --- | --- | --- |
|  | K303U | K312K | K304X |
| Pramipexole 2HCl•H$_2$O | 1.0 | 1.0 | 1.0 |
| Ionic liquid: | | | |
| Isostearic acid (C18) | 2.1 | 2.1 | 2.1 |
| Oleic acid (C18) | 2.1 | 2.1 | 2.1 |
| DIPA | 1.8 | 0.95 | |
| TEA | | 0.95 | 2.0 |
| Skin permeation rate: | 3.63 | 4.27 | 1.47 |
| After 4 hr (µg/cm$^2$ · hr) | (2.5 times) | (2.9 times) | (1.0) |
| Skin permeation amount: | 27.9 | 29.3 | 13.5 |
| After 8 hr (µg/cm$^2$) | (2.1 times) | (2.2 times) | (1.0) |

As shown in Table 13 above, a positive correlation was demonstrated between skin permeation rate and skin permeation amount and similar behavior was indicated. With respect to skin permeation rate, in the same manner as Example 2, the use of strongly basic diisopropanolamine was shown to more strongly promote percutaneous absorption of pramipexole. Moreover, in the case of using triethanolamine and diisopropylamine at a weight ratio of 1:1, the effect of diisopropylamine was dominant, and additive effects with triethanolamine were not demonstrated.

Furthermore, in a relative comparison of test no. K303U with test no. K304X, although skin permeation rate was 2.5 times greater, skin permeation amount was 2.1 times greater. Namely, in order to evaluate the percutaneous absorption promoting effect (in the case of skin permeation being the rate-determining factor) of a fatty acid-based ionic liquid, evaluating percutaneous absorption promoting effect (in the case of skin permeation being the rate-determining factor) on the basis of skin permeation rate was indicated to enable the evaluation to be made with better sensitivity.

As was previously described, the reason for skin permeation rate and skin permeation amount not increasing by the same multiple is thought to be because nearly all of the drug ended up being released from the vicinity of the surface of the plaster that contacts the skin in the 8th hour after application, and that a time lag (releasability of drug from the plaster) gradually begins to have an effect since the drug is released from inside the plaster. Therefore, the following Table 14 results when skin permeation amount is also reevaluated based on values measured in the 4th hour after application.

TABLE 14

|  | Test No. | | |
| --- | --- | --- | --- |
|  | K303U | K312K | K304X |
| Pramipexole 2HCl•H$_2$O | 1.0 | 1.0 | 1.0 |
| Ionic liquid: | | | |
| Isostearic acid (C18) | 2.1 | 2.1 | 2.1 |
| Oleic acid (C18) | 2.1 | 2.1 | 2.1 |
| DIPA | 1.8 | 0.95 | |
| TEA | | 0.95 | 2.0 |
| Skin permeation rate: | 3.63 | 4.27 | 1.47 |
| After 4 hr (µg/cm$^2$ · hr) | (2.5 times) | (2.9 times) | (1.0) |
| Skin permeation amount: | 8.23 | 11.91 | 3.47 |
| After 8 hr (µg/cm$^2$) | (2.4 times) | (3.4 times) | (1.0) |

As shown in Table 14 above, the correlation between skin permeation amount in the 4th hour after application and skin permeation rate increased even more. This indicates that, in the case of examining the rate-determining factor of skin absorption (such as in the case of evaluating percutaneous absorption of a liquid composition), evaluating the amount of skin permeation of a drug in the 4th hour after application makes it possible to examine preparation formulation. The effect of releasability of drug from the plaster can also not be ignored when evaluating skin permeation amount beyond 8 hours after application.

Example 8

Effect of Filler on Skin Permeation Rate

As was indicated in Example 3, since the addition of a filler in the form of a powder to the plaster results in the formation of release channels for an ionic liquid solution containing a drug dispersed in the plaster, the drug is thought to be released more easily from the plaster. Namely, if the release of a drug is favorable, since the drug absorption becomes the rate-determining factor of skin absorption, if the compositions of the ionic liquid and solvent are the same, skin permeation rates ought to be the same. Namely, in order to evaluate the effect of filler, evaluating on the basis of skin permeation rate was thought to be appropriate. Therefore, skin permeation rate was calculated from the experimental results of Example 3, and a summary thereof is shown in the following Table 15 together with the results of Table 3.

TABLE 15

|  | Test No. | | | |
| --- | --- | --- | --- | --- |
|  | K300R | K301S | K312J | K301T |
| Pramipexole 2HCl•H$_2$O | 1.0 | 1.0 | 1.0 | 1.0 |
| Filler: | | | | |
| Soft silicic anhydride | | 3.0 | 1.5 | |
| Ceolus | | | 1.5 | 3.0 |
| Skin permeation amount: | 23.8 | 24.4 | 27.3 | 33.8 |
| After 8 hr (µg/cm$^2$) | (1.0) | (1.0 time) | (1.1 times) | (1.4 times) |
| Skin permeation amount: | 6.41 | 4.98 | 9.73 | 10.37 |
| After 4 hr (µg/cm$^2$) | (1.0) | (0.8 times) | (1.5 times) | (1.6 times) |
| Skin permeation rate: | 2.64 | 2.25 | 3.84 | 4.30 |
| After 4 hr (µg/cm$^2$ · hr) | (1.0) | (0.9 times) | (1.5 times) | (1.6 times) |

As observed in test nos. K300R and K301S of Table 15 above, even if silicic anhydride is added and drug release channels are formed in the plaster to facilitate drug release, there is no improvement in drug releasability. On the other hand, as indicated in test nos. K312J and K301T, in the case of adding crystalline cellulose (Ceolus) and forming drug release channels in the plaster, drug releasability is improved and skin permeation amount and skin permeation rate are enhanced by about 1.5 times. In this manner, an organic filler in the manner of crystalline cellulose was indicated to be preferable for demonstrating the effect of adding filler. In addition, additive effects were determined to not be observed in a combination of organic filler in the manner of crystalline cellulose and inorganic filler in the manner of silicic anhydride, and the effect of organic filler in the manner of crystalline cellulose was determined to be dominant.

Example 9

Effect of Plaster (SIS and Terpene Resin) on Skin Permeation Rate

As indicated in Examples 4 and 5, the ease of release of drug from plaster differs depending on the content and composition of the plaster. Therefore, in order to evaluate releasability of drug from plaster, the content and composition of the plaster were reevaluated on the basis of skin permeation rate. Namely, skin permeation rate was calculated from the results of Examples 4 and 5, and a summary thereof is shown in the following Table 16 together with the results of Table 8 of Example 5.

TABLE 16

| Test No. | K308E | K308D | K304Y | K303U | K305B | K308C | K308F |
|---|---|---|---|---|---|---|---|
| Pramipexole 2HCl•H$_2$O | 1.0 | 1.0 | 1.0 | 1.0 | 1.0 | 1.0 | 1.0 |
| Plaster: | | | | | | | |
| SIS | 21.0 | 21.0 | 18.0 | 18.0 | 15.0 | 15.0 | 12.0 |
| Terpene resin | 21.0 | 7.0 | 12.0 | 6.0 | 15.0 | 5.0 | 12.0 |
| (SIS + resin) | 42.0 | 28.0 | 30.0 | 24.0 | 30.0 | 20.0 | 24.0 |
| Liquid paraffin | 27.5 | 41.5 | 39.5 | 45.5 | 39.5 | 49.5 | 45.5 |
| Skin permeation amount: After 8 hr (μg/cm$^2$) | 16.4 | 29.6 | 29.0 | 27.9 | 35.6 | 31.6 | 39.1 |
| Skin permeation amount: After 4 hr (μg/cm$^2$) | 4.1 | 11.3 | 10.1 | 8.2 | 12.8 | 15.9 | 19.2 |
| Skin permeation rate: After 4 hr (μg/cm$^2$ · hr) | 1.63 | 4.57 | 4.25 | 3.63 | 5.16 | 5.48 | 6.65 |

As shown in Table 16 above, when evaluating the composition and content of plaster based on skin permeation rate, since the structure of the matrix becomes smaller as the content of elastomer in the form of SIS decreases, the drug is released more easily. In addition, even if the content of SIS is the same, drug is released more easily in the case of a high content of terpene resin or high content of liquid paraffin.

On the basis of the above, the total amount of elastomer (SIS) and tackifier (terpene resin) in the plaster is preferably 30% by weight or less, and an elastomer content within the range of 8% by weight to 15% by weight and an amount of tackifier within the range of 1/3 to 1 based on the amount of elastomer were indicated to be preferable for improving drug releasability in the same manner as the conclusion of Example 5. In addition, the content of liquid paraffin was indicated to preferably be about 30% by weight to 50% by weight and more and more preferably about 40% by weight to 50% by weight.

Example 10

Added Amount of Ionic Liquid Preferable for Skin Permeation Rate

In Example 6, the range of the preferable added amount of ionic liquid for which skin absorption of drug serves as the controlling factor was evaluated instead of releasability of drug from the plaster by evaluating the correlation between the added amount of ionic liquid and the skin permeation amount of pramipexole. In the present example, in order to use skin absorption of drug as an evaluation criterion, skin permeation rate was calculated from the results of Example 6 and a summary thereof is shown in the following Table 17 together with the results of Table 9 of Example 6.

TABLE 17

| Test No. | K314V | K314W | K315Y | K303U | K315Z | K314X |
|---|---|---|---|---|---|---|
| Pramipexole 2HCl•H$_2$O | 1.0 | 1.0 | 1.0 | 1.0 | 1.0 | 1.0 |

TABLE 17-continued

| Test No. | K314V | K314W | K315Y | K303U | K315Z | K314X |
|---|---|---|---|---|---|---|
| Ionic liquid: | | | | | | |
| Isostearic acid (C18) | 0.25 | 0.50 | 1.05 | 2.1 | 4.15 | 5.15 |
| Oleic acid (C18) | 0.25 | 0.50 | 1.05 | 2.1 | 4.15 | 5.15 |
| DIPA | 0.22 | 0.45 | 0.9 | 1.8 | 3.6 | 4.50 |
| Liquid paraffin | 50.78 | 50.05 | 48.5 | 45.5 | 39.6 | 36.7 |
| Skin permeation amount: After 8 hr (μg/cm$^2$) | 4.4 | 2.7 | 7.2 | 27.9 | 35.7 | 42.4 |
| Skin permeation | 1.90 | 0.91 | 1.88 | 8.23 | 13.2 | 16.3 |

TABLE 17-continued

| Test No. | K314V | K314W | K315Y | K303U | K315Z | K314X |
|---|---|---|---|---|---|---|
| amount: After 4 hr (µg/cm²) | | | | | | |
| Skin permeation rate: After 4 hr (µg/cm²·hr) | 0.59 | 0.30 | 0.77 | 3.63 | 5.34 | 6.35 |

As shown in test nos. K314V to K315Y of Table 17 above, if the added amount of ionic liquid is excessively low for the same composition of ionic liquid, skin permeation rate remains at a constant low value. This indicates that the release of drug from the plaster is the rate-determining factor. For this reason, it was determined from the results of Table 17 above that unless the content of ionic liquid in the tape preparation is about 5% by weight or more, the release of drug easily becomes the rate-determining factor. In addition, if the content of ionic liquid exceeds about 12% by weight and reaches about 15% by weight, the effect of the release of drug being the rate-determining factor diminishes and the rate-determining factor of skin absorption was determined to be the controlling factor. The amount of ionic liquid is required to be about 0.2 parts by weight or more based on a value of 1 part by weight for the amount of plaster (total amount of SIS and terpene resin), and an amount of 0.7 parts by weight was thought to be adequate. Thus, the content of ionic liquid is preferably about 0.2 parts by weight to 0.7 parts by weight based on a value of 1 part by weight for the amount of plaster.

Example 11

Effect of Filler on Drug Skin Permeation Ratio

As indicated in Test Example 1, the skin permeation amount of a drug is determined by measuring the amount of drug that exudes into the receptor fluid of a Franz diffusion cell as the permeated amount thereof. Thus, the skin permeation ratio of a drug was represented as a percentage by measuring how much of the drug content of a tape preparation adhered to a Franz diffusion cell migrates to the side of the receptor fluid.

The skin permeation ratios at various times after applying test nos. K300R and K301 T of Example 3 (representing how much of the drug of a transdermal patch permeates into the receptor fluid in terms of a percentage) are shown in the following Table 18 and FIG. 6.

TABLE 18

| Test No. | Immediately after application | 4 hours after | 8 hours after | 12 hours after | 20 hours after | 24 hours after |
|---|---|---|---|---|---|---|
| K300R | 0.0% | 3.1% | 11.3% | 18.2% | 28.2% | 31.7% |
| K301T | 0.0% | 4.9% | 16.1% | 24.4% | 35.3% | 38.9% |

Figure 6:
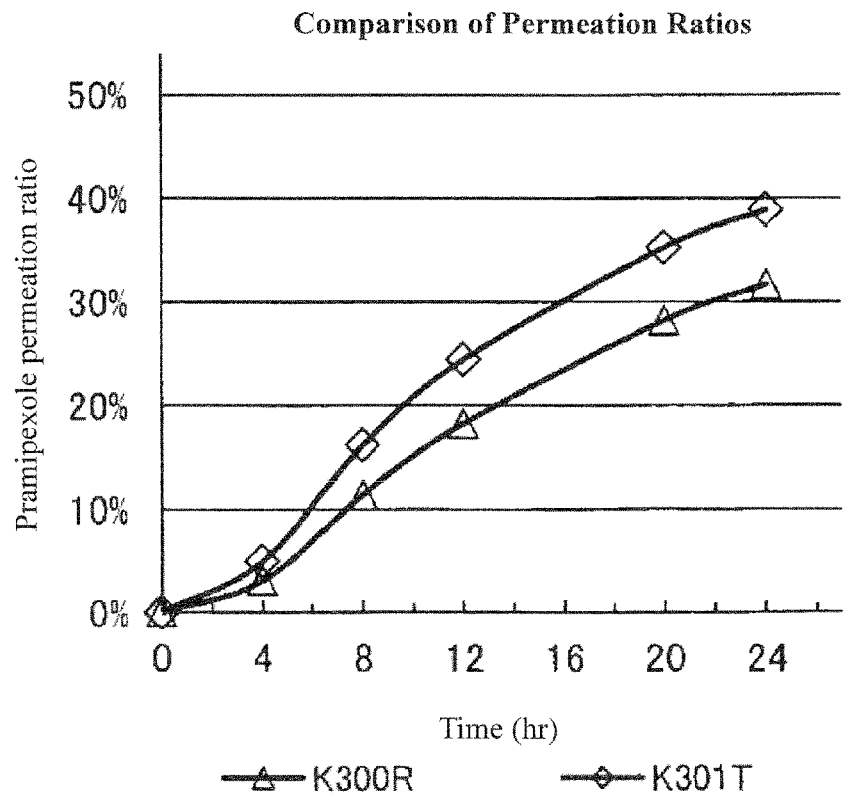
FIG. 6 is a graph representing skin permeation ratios of a drug at various times after application according to the presence or absence of filler based on the aforementioned test nos. K300R and K301T. Drug permeation ratio refers to the percentage obtained by dividing the amount of drug that exuded into the receptor fluid of a Franz diffusion cell by the amount of drug contained in the applied tape. During the 24th hour after application, 30% to 40% of the pramipexole in the tape preparation was indicated to have been released into the receptor fluid. A difference in permeation ratio of about 10% was indicated to be present depending on the presence or absence of filler. The production of a tape preparation to which a filler has been added in this manner was indicated to facilitate release of pramipexole from within the plaster and improve skin permeation ratio of the drug.

As indicated in Table 18 above and FIG. 6, when a comparison was made between K300R in which a filler (Ceolus) was not present and K301T in which a filler (Ceolus) was present, skin permeation ratio increased by nearly about 10% for K301T in which filler was present. Namely, when filler is added, pramipexole is more easily released from within the plaster and drug concentration on the skin is maintained at a high level. As a result, skin permeation ratio of the drug becomes high.

If filler is added, releasability of drug from the plaster increases about 1.5 times as indicated in Example 3. This finding is also supported by the skin permeation ratio of pramipexole. Namely, during the time from 4 to 12 hours after application, skin permeation ratio increases about 1.5 times if filler is added. This indicates that releasability of drug from the plaster increases when filler is added, thereby resulting in an increase in the amount of drug supplied to the skin.

As indicated in Table 18 above, the addition of filler making it possible for nearly 40% of drug contained in the tape preparation to permeate the skin is considered to be a revolutionary finding.

Furthermore, when considering material balance of the drug in the tape preparation, although the majority of the drug permeates to the side of the receptor fluid, a portion of the drug remains in the skin. Therefore, in order to estimate the amount of drug that remains in the skin, a comparison was made between the skin permeation amount at 0 to 2 hours and the skin permeation amount at 2 to 4 hours of the aforementioned test nos. K300R and K301T. The results are shown in FIG. 5.

Figure 5:
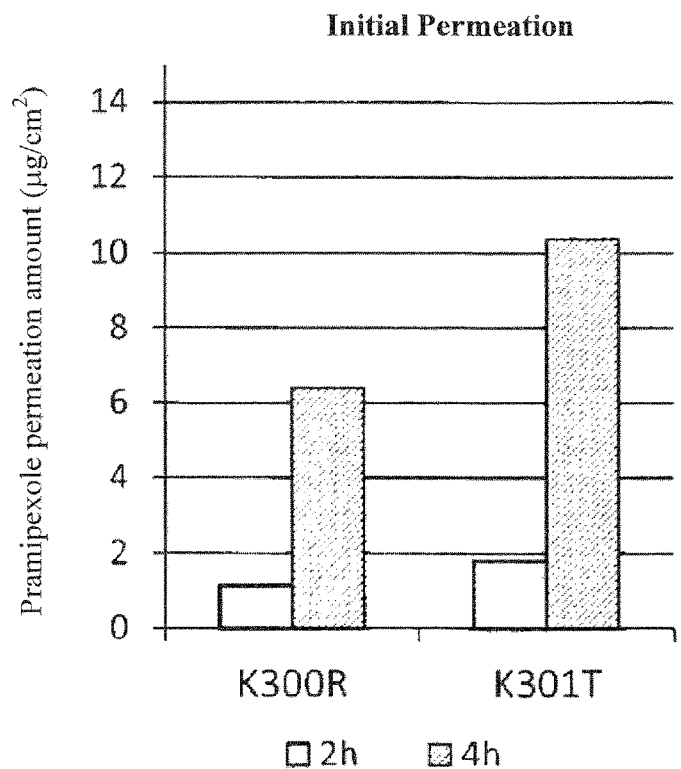
FIG. 5 is a graph representing the skin permeation amounts of drugs at 0 to 2 hours and 2 to 4 hours after application according to the presence or absence of a filler based on the samples of test nos. K300R and K301T of Example 3. Releasability of drug from the plaster clearly differed depending on the presence or absence of filler. Namely, since releasability of drug into the skin was high in the case of the sample to which a filler was added (test no. K301T), this sample demonstrated a higher skin permeation amount than the sample to which a filler was not added (test no. K300R) starting soon after application.

As shown in FIG. 5, the reason for the large difference between skin permeation amounts at 0 to 2 hours and skin permeation amounts at 2 to 4 hours is thought to be due to the time lag of skin permeation of the drug and the drug not being released to the side of the receptor fluid until a certain amount of drug accumulates in the skin and overflows. Therefore, if the difference between skin permeation amounts at 0 to 2 hours and skin permeation amounts at 2 to 4 hours is hypothesized to be equivalent to the amount of drug that accumulates in the skin, then the residual amount of drug in the skin is estimated to be about 5 µg/cm² to 9 µg/cm². If this is the case, then nearly about 3% of the drug remains in the skin.

On the basis of the above, in the pramipexole tape preparation of the present invention, about 35% of the drug migrated into the skin in test no. K300R not containing filler. In addition, about 45% of the drug is presumed to have migrated into the skin in test no. K301T to which filler was added.

Test Example 1

Test for Evaluating Percutaneous Absorption Using Franz Diffusion Cell

Approximately 3 cm² (about 210 µg as pramipexole) were cut from each sample of the aforementioned Example 1 followed by carrying out a test for evaluating percutaneous absorption in the manner indicated below using a Franz diffusion cell (permeation surface area: 1 cm², receptor fluid volume: 8 mL) at a testing temperature of 32° C.

(1) Rat skin: Commercially available excised abdominal skin of 5-week-old Wistar rat (male) was used.
(2) Receptor fluid: Mixture of physiological saline and ethanol (9:1)
(3) Measurement of permeated drug concentration: HPLC (260 nm to 266 nm)

The aforementioned rat abdominal skin (source: 5-week-old Wistar rat (male)) was clamped in a vertical diffusion cell (effective diffusion area: 1 cm²), the samples cut to about 3 cm² described in Tables 1 to 8 were adhered to the horny layer of the skin, and the physiological saline/ethanol solution (9:1) was applied to the dermal layer of the skin.

100 μL aliquots of the receptor fluid were sampled at 2, 4, 6, 8, 12, 20, 22 and 24 hours after the start of the experiment, the concentration of drug that eluted by permeating the skin was measured, and the cumulative permeated amount of drug was measured at each time. In addition, the skin permeation rate of the drug at each time was calculated by dividing the difference between the drug permeation amount at each time and the drug permeation amount at the time immediately prior thereto by elapsed time. Those results are shown in Tables 1 to 18 and FIGS. 1 to 4. As a result, the degree of percutaneous absorption between each preparation sample was able to be evaluated.

INDUSTRIAL APPLICABILITY

The tape preparation of the present invention incorporates a fatty acid-based ionic liquid, a divalent alcohol and a fatty acid ester in order to contain poorly soluble and highly crystalline pramipexole in an organic solvent, resulting in a nonaqueous tape preparation that is both stable and demonstrates superior percutaneous absorption. Thus, the problems of preparation discoloration and lack of stability of the active ingredient associated with conventional aqueous tape preparations are able to be solved, and a tape preparation can be provided that can be used practically as a tape preparation for treatment of Parkinson's disease using pramipexole hydrochloride.

The invention claimed is:

1. A tape preparation, comprising:
   pramipexole or a pharmacologically acceptable salt thereof,
   a C14-C18 fatty acid-based ionic liquid comprising diisopropanolamine oleate and/or diisopropanolamine isostearate,
   a divalent alcohol,
   a fatty acid ester, and
   a plastering material comprising an elastomer and/or tackifier,
   wherein the content of the C14-C18 fatty acid-based ionic liquid is at least 0.2 parts by weight based on a value of 1 for the amount of the plastering material.

2. The tape preparation according to claim 1, wherein the divalent alcohol is one or more divalent alcohols selected from propylene glycol, polyethylene glycol and 1,3-butanediol.

3. The tape preparation according to claim 1, wherein the divalent alcohol is propylene glycol.

4. The tape preparation according to claim 1, wherein the fatty acid ester is one or more fatty acid esters selected from diethyl sebacate, isopropyl myristate, propylene carbonate and diisopropyl adipate.

5. The tape preparation according to claim 1, wherein the fatty acid ester is diethyl sebacate and/or isopropyl myristate.

6. The tape preparation according to claim 1, further comprising a filler.

7. The tape preparation according to claim 6, wherein the filler is an organic filler.

8. The tape preparation according to claim 6, wherein the organic filler is crystalline cellulose.

9. The tape preparation according to claim 1, wherein the pramipexole or pharmacologically acceptable salt thereof is pramipexole dihydrochloride.

10. The tape preparation according to claim 1, wherein the content of the C14-C18 fatty acid-based ionic liquid is 0.2 parts by weight to 0.7 parts by weight based on a value of 1 for the amount of the plastering material.

11. The tape preparation according to claim 1, wherein the C14-C18 fatty acid-based ionic liquid comprises diisopropanolamine oleate.

12. The tape preparation according to claim 1, wherein the C14-C18 fatty acid-based ionic liquid comprises diisopropanolamine isostearate.

13. The tape preparation according to claim 1, wherein the C14-C18 fatty acid-based ionic liquid comprises diisopropanolamine oleate and diisopropanolamine isostearate.

14. The tape preparation according to claim 1, wherein the plastering material comprises one or more elastomers selected from the group consisting of styrene-butadiene-styrene block copolymer, styrene-isoprene block copolymer, styrene-isoprene-styrene block copolymer (SIS), styrene-ethylene/butylene block copolymer, styrene-ethylene/butylene-styrene block copolymer, styrene-ethylene/propylene block copolymer, styrene-ethylene/propylene-styrene block copolymer, styrene-isobutylene block copolymer and styrene-isobutylene-styrene block copolymer.

15. The tape preparation according to claim 1, wherein the plastering material comprises one or more tackifiers selected from the group consisting of rosin-based resins, terpene resins, coumarone-indene resins, petroleum-based resins, terpene-phenol resins and alicyclic saturated hydrocarbon resins.

* * * * *